United States Patent
Forth et al.

(10) Patent No.: US 10,307,084 B2
(45) Date of Patent: Jun. 4, 2019

(54) IDENTIFYING FALL RISK USING MACHINE LEARNING ALGORITHMS

(71) Applicant: iShoe, Inc., Houston, TX (US)

(72) Inventors: Katharine Forth, Houston, TX (US); Erez Lieberman Aiden, Houston, TX (US)

(73) Assignee: ZIBRIO INC., Houston, TX (US)

( * ) Notice: Subject to any disclaimer, the term of this patent is extended or adjusted under 35 U.S.C. 154(b) by 346 days.

(21) Appl. No.: 15/197,388

(22) Filed: Jun. 29, 2016

(65) Prior Publication Data

US 2017/0000387 A1    Jan. 5, 2017

Related U.S. Application Data

(60) Provisional application No. 62/186,366, filed on Jun. 30, 2015.

(51) Int. Cl.
*A61B 5/11*     (2006.01)
*G06N 99/00*    (2019.01)
(Continued)

(52) U.S. Cl.
CPC .......... *A61B 5/1117* (2013.01); *A61B 5/1036* (2013.01); *A61B 5/4023* (2013.01);
(Continued)

(58) Field of Classification Search
CPC ... A61B 5/1117; A61B 5/4023; A61B 5/1036; A61B 5/7275; A61B 5/7264;
(Continued)

(56) References Cited

U.S. PATENT DOCUMENTS

| 4,738,269 A | 4/1988 | Nashner |
| 5,052,406 A | 10/1991 | Nashner |

(Continued)

FOREIGN PATENT DOCUMENTS

| JP | 2010/508945 A | 3/2010 |
| WO | 2007102708 A1 | 9/2007 |

(Continued)

OTHER PUBLICATIONS

Rasku et al: "Recognition of balance signals between healthy subjects and otoneurological patients with hidden Markov models", Biomedical Signal Processing and Control, vol. 2, No. 1, Jan. 1, 2007, pp. 1-8, Elsevier, Amsterdam, NL.

*Primary Examiner* — Jonathan Han
(74) *Attorney, Agent, or Firm* — Norton Rose Fulbright US LLP

(57) ABSTRACT

A person's fall risk may be determined based on machine learning algorithms. The fall risk information can be used to notify the person and/or a third party monitoring person (e.g. doctor, physical therapist, personal trainer, etc.) of the person's fall risk. This information may be used to monitor and track changes in fall risk that may be impacted by changes in health status, lifestyle behaviors or medical treatment. Furthermore, the fall risk classification may help individuals be more careful on the days they are more at risk for falling. The fall risk may be estimated using machine learning algorithms that process data from load sensors by computing basic and advanced punctuated equilibrium model (PEM) stability metrics.

20 Claims, 17 Drawing Sheets

(51) Int. Cl.
    *A61B 5/00*     (2006.01)
    *G06F 19/00*     (2018.01)
    *A61B 5/103*     (2006.01)
    *G16H 50/30*     (2018.01)

(52) U.S. Cl.
    CPC .......... *A61B 5/7267* (2013.01); *A61B 5/7275* (2013.01); *G06F 19/00* (2013.01); *A61B 5/0022* (2013.01); *A61B 5/1116* (2013.01); *A61B 5/6887* (2013.01); *A61B 2503/08* (2013.01); *A61B 2562/0252* (2013.01); *G16H 50/30* (2018.01)

(58) Field of Classification Search
    CPC ..... A61B 5/1116; A61B 5/1038; A61B 5/112; G08B 21/0446; G08B 21/043; A63B 26/003; G16H 50/30
    USPC ......... 600/300, 587, 595; 702/139, 152, 153
    See application file for complete search history.

(56) References Cited

U.S. PATENT DOCUMENTS

| | | | |
|---|---|---|---|
| 5,388,591 A | 2/1995 | De Luca et al. | |
| 5,627,327 A | 5/1997 | Zanakis | |
| 5,830,158 A | 11/1998 | Zanakis | |
| 5,919,149 A | 7/1999 | Alum | |
| 5,987,982 A | 11/1999 | Wenman et al. | |
| 6,063,046 A | 5/2000 | Allum | |
| 6,389,883 B1* | 5/2002 | Berme | A61B 5/4023 73/65.01 |
| 7,612,681 B2 | 11/2009 | Azzaro et al. | |
| 7,682,308 B2 | 3/2010 | Hendrich | |
| 8,011,229 B2 | 9/2011 | Lieberman et al. | |
| 8,152,744 B2 | 4/2012 | Mukumoto | |
| 8,206,325 B1 | 6/2012 | Najafi et al. | |
| 8,405,510 B2 | 3/2013 | Shieh et al. | |
| 8,529,448 B2 | 9/2013 | McNair | |
| 8,773,256 B2 | 7/2014 | Ten Kate et al. | |
| 2001/0032059 A1* | 10/2001 | Kelly, Jr. | A61B 5/0002 702/150 |
| 2009/0137933 A1* | 5/2009 | Lieberman | A61B 5/1036 600/595 |
| 2010/0049096 A1* | 2/2010 | Ten Kate | G08B 21/0446 600/595 |
| 2011/0152727 A1* | 6/2011 | Ten Kate | A61B 5/1117 600/595 |
| 2011/0166488 A1* | 7/2011 | Miyake | A61B 5/112 601/34 |
| 2011/0313714 A1 | 12/2011 | Lieberman et al. | |
| 2012/0095722 A1 | 4/2012 | Ten Kate | |
| 2012/0119904 A1 | 5/2012 | Coleman Boone et al. | |
| 2012/0253233 A1 | 10/2012 | Greene et al. | |
| 2013/0246088 A1* | 9/2013 | Huster | G06Q 10/0635 705/2 |
| 2014/0024972 A1 | 1/2014 | Greene | |
| 2014/0100487 A1 | 4/2014 | McNair | |
| 2014/0330171 A1 | 11/2014 | Pan et al. | |
| 2015/0005674 A1 | 1/2015 | Schindler et al. | |

FOREIGN PATENT DOCUMENTS

| | | |
|---|---|---|
| WO | 2008/059418 A1 | 5/2008 |
| WO | 2014158698 A1 | 10/2014 |
| WO | 2014210344 A1 | 12/2014 |
| WO | 2015/003211 A1 | 1/2015 |

\* cited by examiner

IDENTIFYING FALL RISK USING MACHINE LEARNING ALGORITHMS

CROSS-REFERENCE TO RELATED PATENT APPLICATIONS

This application claims the benefit of priority of U.S. Provisional Patent Application No. 62/186,366 to Forth et al. filed on Jun. 30, 2015 and entitled "Method and System for Identifying Balance and Fall Risk," which is hereby incorporated by reference.

FIELD OF THE DISCLOSURE

The instant disclosure relates to machine learning algorithms. More specifically, portions of this disclosure relate to applying machine learning algorithms to determine patient balance or identify patient fall risk.

BACKGROUND

Unintentional falls account for greater than 30,000 annual deaths within the US population. Seniors are most vulnerable to falling and, as a result, suffer more than 300,000 hip fractures a year. Of those who fracture a hip, 50% will never return to their homes. The poor balance that contributes to these fall events often declines for decades in advance of the fall event, yet the conventional method for tackling poor balance is to seek medical diagnostics and interventions only after a fall has occurred or the patient has a very serious balance problem. In fact, the current best predictor of a fall is whether someone has already fallen.

To truly improve the statistics of falls across the country, preventive intervention should be performed in advance of the first fall. Balance is similar to other physical performances, it can be improved with practice and, conversely, deteriorates with disuse. A number of lifestyle and health factors are known to influence one's balance, such as exercise, strength, sleep, cognitive functioning, vitamin D supplements, and medication management. Lifestyle changes to improve balance will take time to build up their protective effect. Measuring balance and fall risk affords the opportunity to detect subtle balance changes that can occur with health and lifestyle adjustments.

The human balance control system is very complex with three or more sensory inputs creating a repertoire of motor outputs, each with differing strategies that are affected by subconscious and conscious control, experience, context, and personality. The circumstances surrounding falling further complicates matters as the source of a fall can be from numerous intrinsic and extrinsic factors. Consequently, predicting falls with a basic measure of balance is insufficient on its own. The added insight and predictive power that machine learning techniques provide for human balance control systems can facilitate a more accurate prediction of falls.

One such machine learning approach is discussed in U.S. Pat. No. 8,011,229. The '229 patent uses Hidden Markov Model techniques for determining postural stability by identifying different postural states from center of pressure (COP) data. COP is the central location of combined pressure from 2 or more pressure or load sensors. The postural states relate to a classification of either static or dynamic. As the names suggest, a static postural state is defined as a dwell region within the COP data wherein sway is constrained to a single equilibrium. While a person is in a static state their body sway is considered under control and the person is more balanced and less likely to fall. A dynamic postural state is defined as sections of COP data that are not constrained to any equilibria and are by definition, unconstrained or uncontrolled. While a person is in a dynamic state they are considered to be "escaping" an equilibrium and are either moving to another equilibrium or falling. The static and dynamic postural states facilitate an assessment of postural stability undocumented before, defining a new model of postural control: the punctuated equilibrium model (PEM). The PEM is defined as periods of stability punctuated by dynamic trajectories. The PEM classification of postural states is particularly applicable for real-time or near-real-time assessment of stability. However, subsequent metrics that quantify the postural states facilitate a determination of instability trends along longer timelines. Measures of postural instability within the PEM are identified as: number of equilibria, equilibria dwell time and size of equilibria.

There are a number of advantages of the PEM approach. Firstly, the technique classifies otherwise uniform data, identifying stable regions and dynamic trajectories, with the latter being viewed as unstable. Threshold functions are described to identify the postural state users are in, whether for real-time identification or long term detection of postural instability. Further, the approach creates relative measures of stability that create independence from height and weight, location of the feet, or known stability boundaries.

While the preceding approach improved insights into postural stability, it is commonly understood that the multifactorial nature of falls means that predicting falls outside of the real-time and near-real-time fall range is difficult to achieve. Despite the development to date, there remains a need for improved postural stability representation.

SUMMARY

Determining a patient's fall risk remains a challenging task. Conventional fall risk indicators are whether an individual has previously fallen. Conventional fall risk assessment tests place the individual at risk, such as by placing the individual into challenging positions and gauging their stability in that position. However, a negative outcome of the test is a fall, and the test is thus not different from the conventional fall risk indicator. The PEM approach may be used for determining fall risk of a patient. Machine learning algorithms may be used to identify combinations of metrics and raw data that are indicative of an individual's fall risk. Because the PEM approach does not place the individual in a risky position, the individual's fall risk can be assessed with little danger to the individual.

According to embodiments of the present invention, there is provided an improved method for balance and fall risk measurement and analysis that comprises the steps of acquiring load data points from at least two or more load sensors, calculating center of pressure (COP) for each data point, and using machine learning algorithms for classifying fall risk based on the calculated COP. One embodiment of the invention includes the Hidden Markov Model as the machine learning algorithm. The method may then include calculating the current postural state, the next postural state and a range of metrics. The metrics can include at least one of the base punctuated equilibrium model (PEM) metrics, and at least one of a set of advanced PEM metrics: time to first equilibrium, equilibria distance, equilibria overlap, percent equilibrium, mean equilibria duration, and directional equilibria.

According to some embodiments of the present invention, there is provided an improved method for balance and fall risk measurement and analysis that comprises the step of calculating the current postural state, the next postural state, and integrating a range of metrics. The metrics can include at least one of the base PEM metrics, and at least one of a set of advanced PEM metrics: time to first equilibrium, equilibria distance, equilibria overlap, percent equilibrium, mean equilibria duration, and directional equilibria, and at least one of the COP basic metrics. An integration of at least one metric from each of the base PEM metrics, advanced PEM metrics, and basic metrics can use one of several possible artificial intelligence techniques for determining the final balance score and fall risk. These approaches include: use of principal component analysis, Bayesian classification, neural network or deep-learning based strategies, and SVMs (support vector machines). In one embodiment, the integration model is a linear combination of stability metrics including at least one metric from each of the base PEM metrics, advanced PEM metrics, and basic metrics. The metrics are transformed to parameter scores on a scale of 1 to 10 and a composite balance score is calculated as a weighted average of the metrics. The range of the composite balance score may also be from 1 to 10. Thresholds may be assigned to the balance score for classifying patients.

The determination of fall risk may be assisted, in some embodiments, by a system that houses load sensors as well as a signal preparation module that captures and transmits load data and, therefore, gathers equilibrium data about a person. The system may be a scale including two or more load sensors that wirelessly transmits load data to a mobile device and then to a data analysis module. In some embodiments, the scale may transmit data over a short-range communications link, such as Bluetooth or to the mobile device, such as a phone, tablet, or laptop computer, which then transmits the data over a long-range communications link, such as a wide area network (WAN) through the Internet to a server with a data analysis module. In some embodiments, the scale may transmit data over a short-range communications link to the mobile device, and the mobile device may include a data analysis module, and the results of the data analysis module may be uploaded to a server for monitoring and/or accessing the data. The data analysis module in a mobile device or server may perform processing of data, such as executing a machine learning algorithm and calculating the balance score and fall risk classification. In some embodiments, the results may be displayed on the system for display, such as with LEDs or an LCD on the scale.

In some embodiments, the system may be a device that houses two or more load sensors, the data analysis module, and a display for outputting the individual's balance and/or fall risk. The device may include a surface upon which an individual can stand comprising two or more load sensors. A data analysis module, such as a processor configured to perform steps for executing a machine learning algorithm, may process data from the two or more load sensors and generate balance information and/or a fall risk classification. Illuminating member of the device may comprise LED lights that illuminate through a semi-transparent top surface creating a glow effect of color that represents the fall risk classification of the user, and LED numbers illuminating through the top surface may display the balance score and weight. The surface device may also include a signal preparation module, which may transmit the load data, balance information, weight, and/or fall risk information to other equipment, such as a mobile device (e.g., a mobile phone, a tablet, a smart watch, a fitness watch, a fitness tracker, a laptop computer) or to a server. The signal preparation module may include communications equipment for communicating over either a short range communications link such as Wi-Fi or Bluetooth to transmit the data to another computer or the Internet or a long range communications link such as 2G, 3G, or 4G cellular communications.

In general, technology described in embodiments herein provides a system and method for determining a person's fall risk and/or composite balance score. The technology may be used, for example, by seniors, athletes, patients, doctors, physical therapists, nurses, astronauts, and/or any person that needs to assess fall risk or postural stability.

The foregoing has outlined rather broadly certain features and technical advantages of embodiments of the present invention in order that the detailed description that follows may be better understood. Additional features and advantages will be described hereinafter that form the subject of the claims of the invention. It should be appreciated by those having ordinary skill in the art that the conception and specific embodiment disclosed may be readily utilized as a basis for modifying or designing other structures for carrying out the same or similar purposes. It should also be realized by those having ordinary skill in the art that such equivalent constructions do not depart from the spirit and scope of the invention as set forth in the appended claims. Additional features will be better understood from the following description when considered in connection with the accompanying figures. It is to be expressly understood, however, that each of the figures is provided for the purpose of illustration and description only and is not intended to limit the present invention.

BRIEF DESCRIPTION OF THE DRAWINGS

For a more complete understanding of the disclosed system and methods, reference is now made to the following descriptions taken in conjunction with the accompanying drawings.

DETAILED DESCRIPTION

In general, aspects of the present invention relate to methods and systems for determining a person's fall risk. The fall risk information can be used to notify the person and/or a third party monitoring person (e.g. doctor, physical therapist, personal trainer, etc.) of the person's fall risk. This information may be used to monitor and track changes in fall risk that may be impacted by changes in health status, lifestyle behaviors or medical treatment. Furthermore, the fall risk classification may help individuals be more careful on the days they are more at risk for falling. This is in contrast to the general guidelines for preventing falls that are unrealistic in their expectation of increased vigilance and attention at all times. Alerting someone to their fall risk level empowers them to take action in the short term, such as to use a cane when the fall risk level is high, or for seeking professional advice for making lifestyle changes for long term improvement of fall risk. In some embodiments, data may be collected over days, weeks and/or months and long-term predictions formed for the individual.

Figure 1:
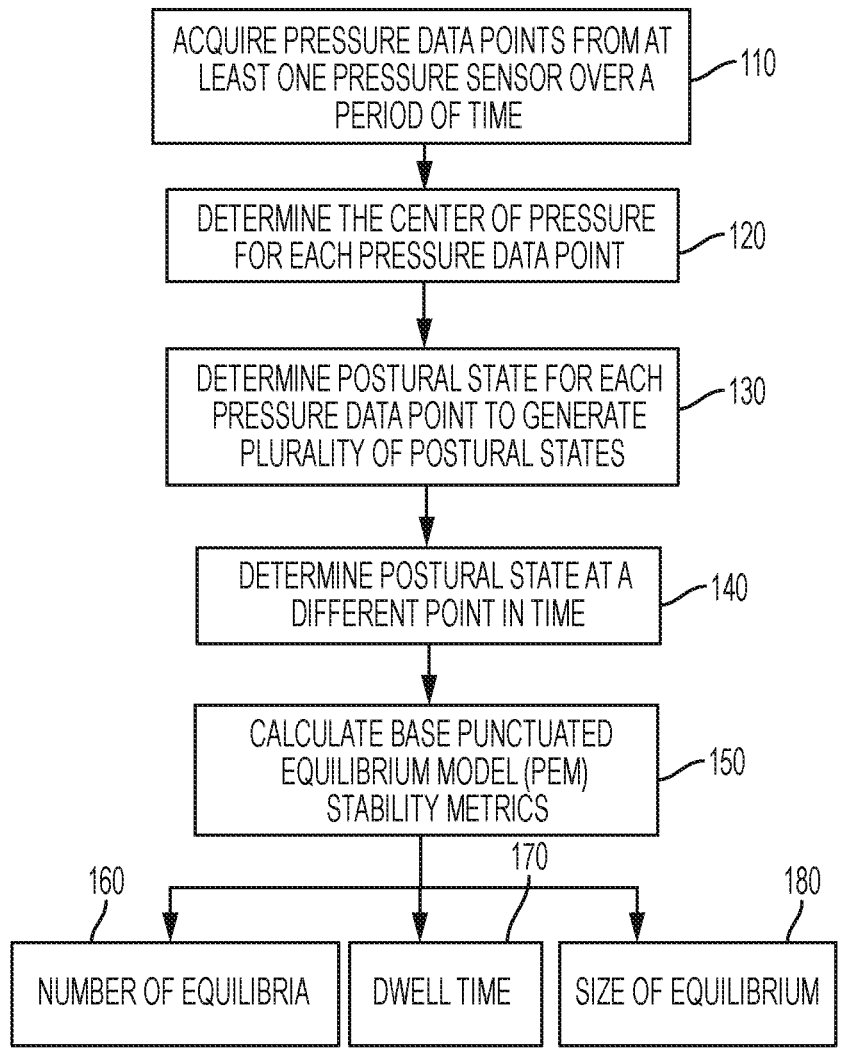
FIG. 1 is a block diagram illustrating a conventional balance assessment method.

FIG. 1 is a block diagram illustrating a conventional method of classifying postural states with a Hidden Markov Model (HMM). HMMs are temporal probabilistic models, modelling a series of states over time. These states are not directly observable, and thus are hidden. However, there is a set of possible observations at each point in time, which may correlate to the true hidden state at that time. Therefore, given a sequence of observations over a period of time, HMMs determine the most likely hidden state.

Conventionally, a HMM may classify postural states from center of pressure (COP) data. COP data may represent the central location of combined pressure from pressure or load sensors over a period of time and associated with a person. Pressure data is acquired from at least one pressure sensor over a period of time 110 and the COP is calculated for each pressure data point 120. A HMM calculation determines the current and/or next postural state 130. The HMM utilizes a set of probabilities for each postural state to determine the next postural state 140. The postural states relate to a classification of either static or dynamic. The static postural state is defined as a dwell region within the COP data wherein sway is constrained to a single equilibrium. While a person is in a static state their body sway is considered under control and the person is more balanced and less likely to fall. A dynamic postural state is defined as sections of COP data that are not constrained to any equilibria and are by definition, unconstrained or uncontrolled. While a person is in a dynamic state they are considered to be "escaping" an equilibrium and are either moving to another equilibrium or falling.

The static and dynamic postural states facilitate a punctuated equilibrium model (PEM) of postural stability. The PEM is defined as periods of stability punctuated by dynamic trajectories. Alerting a person to that transient dynamic and thereby dangerous state can help them take instant action to avoid the imminent fall. Base measures of postural instability from the PEM 150 are identified as: number of equilibria 160, equilibria dwell time 170, and size of equilibria 180. The number of equilibria 160 may include a number of equilibria identified in a time series. The dwell time 170 may include a size of a pentagon or other shape that represents the time spent in that particular equilibrium. The size of equilibria 180 may include an average (or other characteristic such as mean, maximum, or minimum) of each point in the equilibrium to the center of the corresponding equilibrium.

Figure 2:
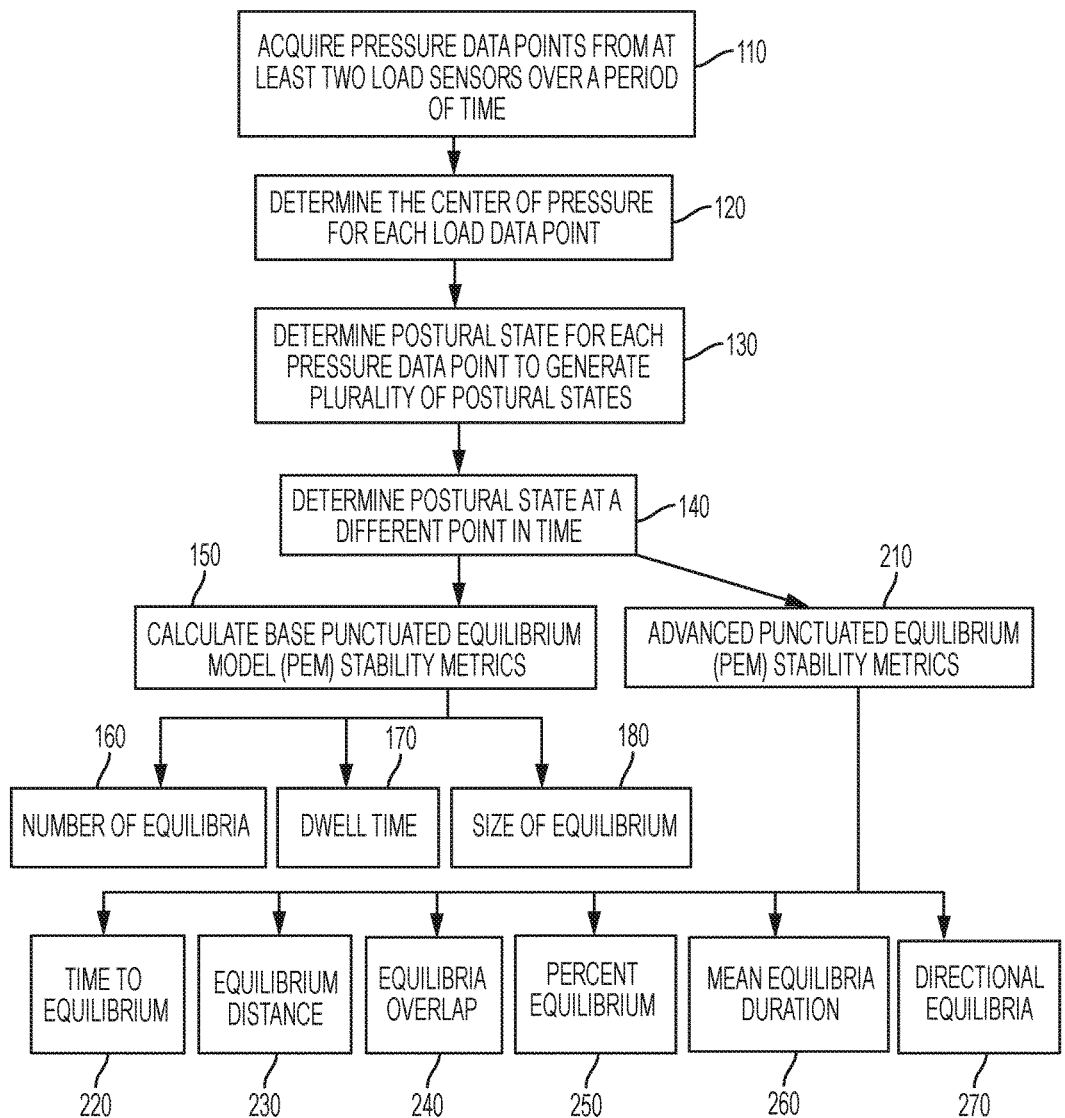
FIG. 2 is a block diagram illustrating a method for determining base punctuated equilibrium model (PEM) stability metrics and advanced PEM metrics according to some embodiments of the disclosure.

Although the base punctuated equilibrium model (PEM) stability metrics 160, 170, and 180 may be sufficient for determining postural states. Additional stability metrics may improve determination of postural states and/or allow for the determination of fall risk and/or classifying an individual's fall risk. Embodiments of the invention use machine learning techniques, such as to classify dynamic and static postural states for a PEM with HMM techniques, using advanced PEM stability metrics. The PEM defines multiple equilibria punctuated by dynamic trajectories of COP data series. The PEM approach creates defined regions and geometric patterns from COP data trajectories. For example, FIG. 2 is a block diagram illustrating a method for determining advanced PEM metrics, including time to equilibrium 220, equilibrium distance 230, equilibrium overlap 240, percent equilibrium 250, mean equilibria duration 260, directional equilibria 270.

In one embodiment of calculation of the advanced PEM metrics, data from at least two load sensors are acquired over a period of time at block 110 and associated with a person. The COP data may be calculated from the load sensor inputs for each load data point 120. This may generate a time series of COP data. A HMM calculation may be used to determine a current and/or next postural state at block 130. The HMM may use a set of probabilities for each postural state to determine a next postural state at block 140. In some embodiments, the HMM calculation determines the next state, the current state, and/or one or more past states (e.g. five, ten). The postural states may relate to a classification of either static or dynamic. The static postural state may be defined as a dwell region within the COP data wherein sway is constrained to a single equilibrium. The classification of the time series for postural state may then allow calculations of base PEM stability metrics 150 as well as advanced PEM stability metrics 210, including time to first equilibrium 220, equilibria distance 230, equilibria overlap 240, percent equilibrium 250, mean equilibria duration 260, and directional equilibria 270. In some embodiments, PEM stability metrics 210 may include time to first equilibrium (e.g., time elapsed before first equilibrium establishment), equilibria distance (e.g., mean distance of center of equilibria to adjacent equilibria centers), equilibria overlap (e.g., percentage of equilibria overlap of equilibria 95% circle in a time series), percent equilibrium (e.g., percent of time spent in equilibrium in a time series), mean equilibria duration (e.g., mean duration of equilibria in a time series), and/or directional equilibria (e.g., weighted number of equilibria by the degree of anterior posterior deviation of the directional vector to adjacent equilibria centers from the medial lateral, X-axis). Additional details regarding the determining the COP data, determining postural states, and determining base PEM stability metrics are described in U.S. Pat. No. 8,011,229 to Lieberman et al, filed on Nov. 26, 2008 and entitled "Determining postural stability," which is hereby incorporated by reference.

Figure 3:
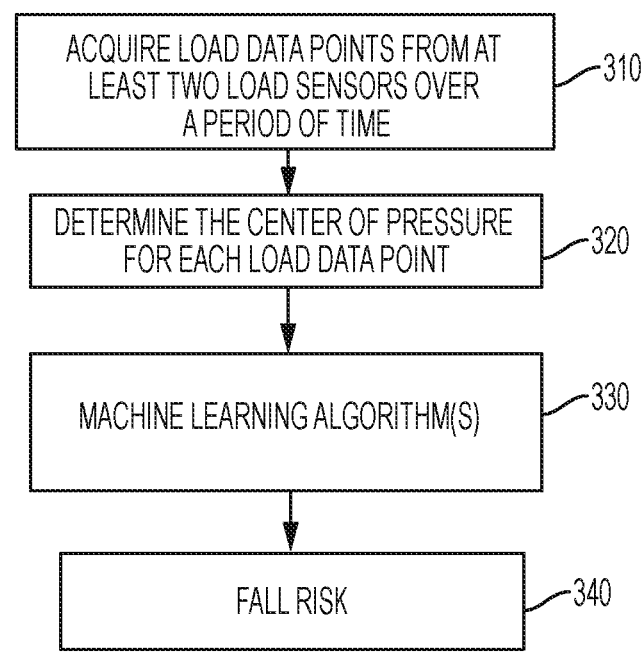
FIG. 3 is a block diagram illustrating a method for determining fall risk using a machine learning algorithm and (center of pressure) COP data according to some embodiments of the disclosure.

FIG. 3 is a block diagram illustrating a method for determining fall risk using a machine learning algorithm and (center of pressure) COP data according to some embodiments of the disclosure. A method for determining fall risk begins at block 310 with acquiring load data points from at least two load sensors over a period of time. Then, at block 320, each load data point may be used to calculate center of pressure (COP) data. Next, at block 330, machine learning algorithms may receive the COP data and calculate, for example, postural states. Then, at block 340, the machine learning algorithms may be used to estimate fall risk and/or classify fall risk. In some embodiments, the machine learning algorithms may be used to classify postural states for calculating subsequent metrics and determine fall risk thresholds at block 340. In other embodiments, the machine learning algorithm may be used to classify fall risk as the objective function, either with or without the preceding determination of postural states. In some embodiments, the estimated fall risk may also be based, in part, on at least one of clinical records, exercise, lifestyle inputs, weight, body fat composition, body mass index, level of hydration, medication consumption, alcohol consumption, sleep, steps per day, exercise, time spent sitting, and/or strength.

Figure 4:
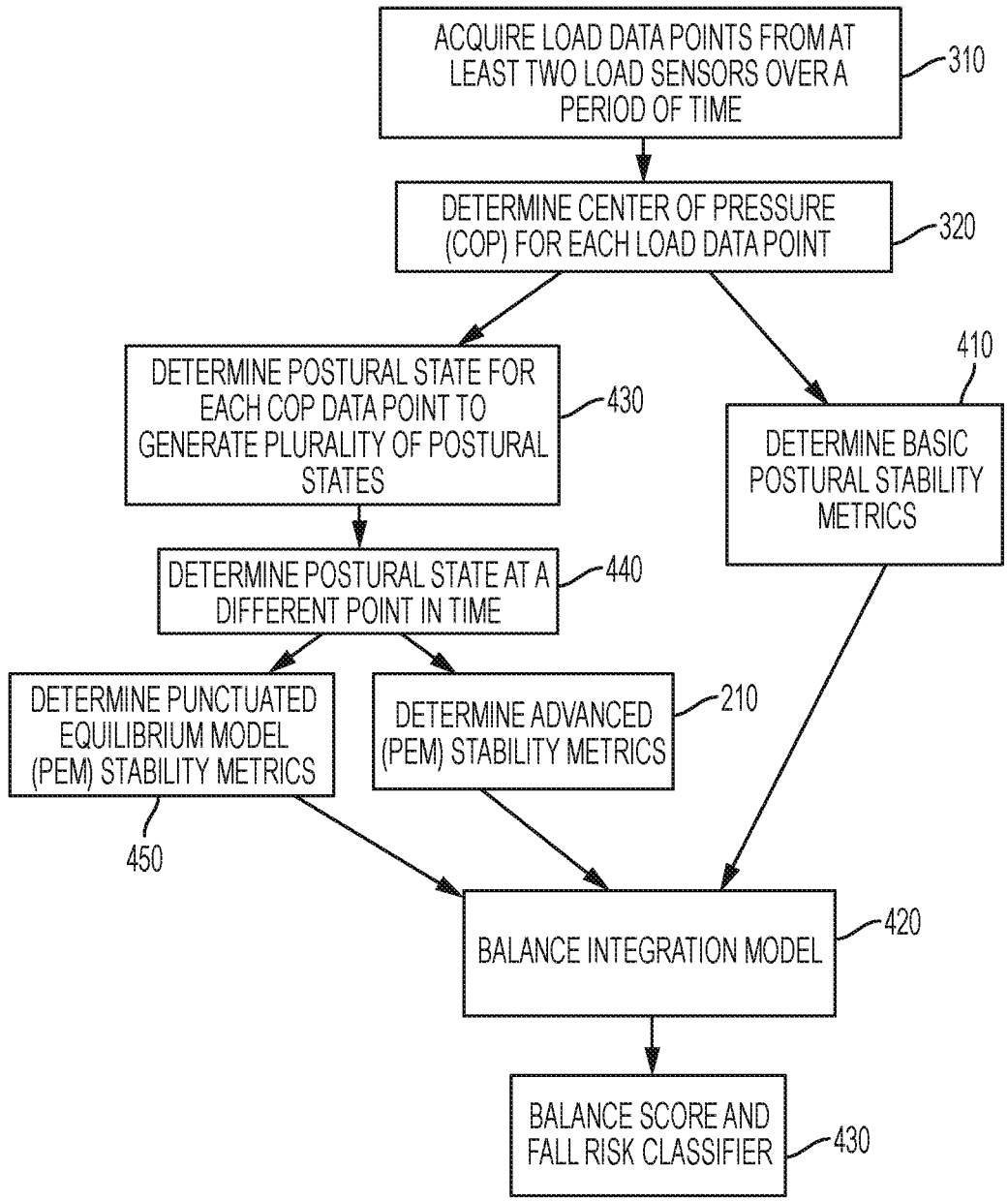
FIG. 4 is a block diagram illustrating a machine learning algorithm for determining balance score and fall risk classification based on data acquired from load sensors according to some embodiments of the disclosure.

FIG. 4 is a block diagram illustrating a machine learning algorithm for determining balance score and fall risk classification based on data acquired from load sensors according to some embodiments of the disclosure. The COP is calculated at block 320 from the load data received at block 310 for each load data point over a period of time. The postural state classification at block 430 classifies two states: static and postural state with HMM techniques. The HMM may utilize a set of probabilities for each postural state to determine the next postural state at block 440. A balance integration model may be determined at block 420 from the base PEM stability metrics calculated at block 450 and the advanced PEM stability metrics 210. For example, a balance score and/or fall risk determination may be made based, in part, on a weighted combination of one or more base PEM stability metrics calculated at block 150 and one or more advanced PEM stability metrics calculated at block 210. In some embodiments, the balance integration module of block 420 may also be based on basic postural stability metrics 410 from an inverted pendulum model (IPM) using one of several possible artificial intelligence techniques. A balance score and/or fall risk classifier may be generated at block 430 from the balance integration model of block 420. Strategies for determining the final balance score include use of principal component analysis, Bayesian classification, neural network or deep-learning based strategies, SVMs (support vector machines), or supervised and unsupervised learning approaches more broadly. In addition to the stability metrics, raw data, such as COP values over time or load values over time, may also be provided to the artificial intelligence. In the case of a neural network, the network can be trained (using training data from individuals with a known fall history) to identify combinations of metrics and raw data indicative of fall risk.

In one embodiment, the balance integration model 420 may be a linear combination of stability metrics including: at least two of the basic PEM metrics 450 combined with at least two of the advanced PEM metrics 210 and at least two of the basic metrics 410 to create a robust representation. The selected metrics may be used to generate a score on a scale of 1 to 10, and for some metrics a logistical function transformation may be necessary. Metrics are then weighted to optimize classification of fall risk, yielding a balance score at Hock 430.

In some embodiments, the method may incorporate a number of input metrics from differing theoretical models. For example, one such model is the IPM that yields basic COP metrics 410 describing the sway around a single point. The metrics include anterior-posterior COP peak sway (e.g., maximum anterior-posterior displacement in a time series), mediolateral COP peak sway (e.g., maximum mediolateral displacement in a time series), standard deviation of mediolateral sway, standard deviation of anterior-posterior sway, the radius of a 95% circle (e.g., radius of the circle that includes 95% of the COP data in a time series) or ellipse (e.g., radius of the ellipse that includes 95% of the COP data in a time series), mean speed of COP (e.g., mean of a COP speed in a time series), root mean squared speed (e.g., root mean square value of the COP speed in a time series), and percentage time above a predetermined speed (e.g., fraction of time series above 0.1 m/s in a time series), standard deviation of mediolateral position in a time series (e.g., stdCopML), standard deviation of anterior-posterior position in a time series (e.g., stdCopAP).

FIG. 5 and FIG. 6 illustrate metrics from both postural stability models, IPM and PEM, respectively. The IPM yield more gross metrics of a single cluster, while the PEM yields finer metrics as these data have been further classified to multiple clusters.

Figure 5A:
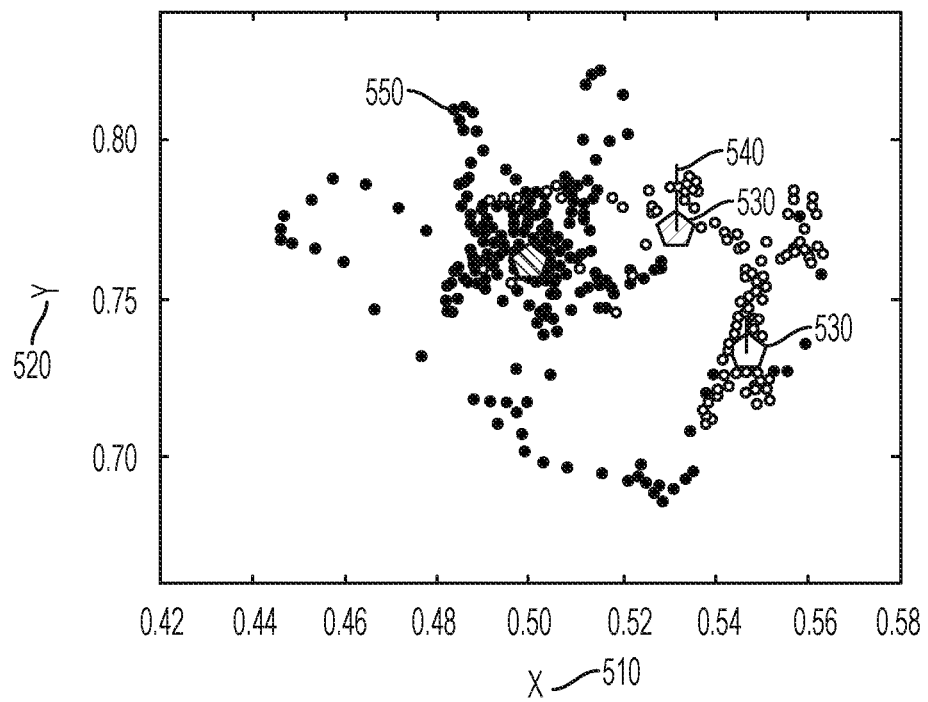
FIG. 5A is a stabilogram of center of pressure (COP) data classified into punctuated equilibrium with Hidden Markov Model techniques according to one embodiment of the disclosure as applied to one individual's data.

FIG. 5A is a stabilogram of center of pressure (COP) data classified into punctuated equilibrium with Hidden Markov Model techniques according to one embodiment of the disclosure as applied to one individual's data. The x axis is the COP mediolateral sway 510, 0 is the left foot and 1 is the right foot. The y axis is the COP anterior-posterior sway 520 with 1 being anterior direction and 0 the posterior direction. The x and y axis relate to the distance of sway. The different color shades represent different defined equilibria with a pentagon 530 of matching color overlaying the clustered regions of static equilibrium. The size of the pentagon represents the relative size of that equilibrium 530. The larger the pentagon the longer the person remained in control in that equilibrium. The line within the pentagon 540 represents the mean distance each COP point is from the equilibrium center of the equilibrium it is associated. The points with an outer black line represent points in a dynamic state 550 and thus, have no equilibrium or pentagon associated.

Figure 5B:
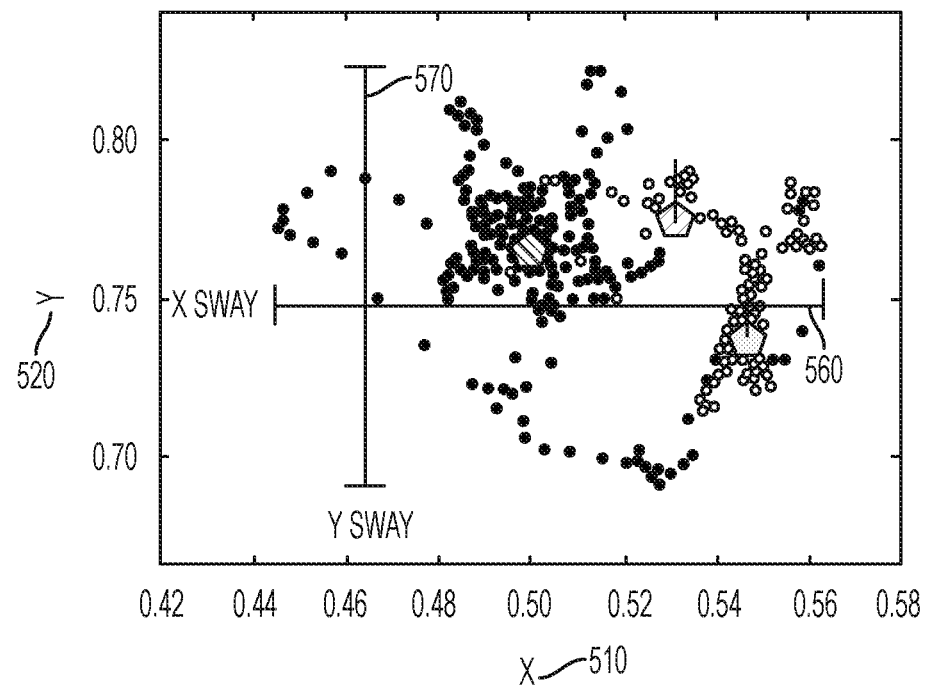
FIG. 5B is the stabilogram of FIG. 5A with the basic metrics of mediolateral peak sway (XSWAY) and anterior-posterior peak sway (YSWAY) overlaid.

FIG. 5B is the stabilogram of FIG. 5A with the basic metrics of mediolateral peak sway (XSWAY) and anterior-posterior peak sway (YSWAY) overlaid. The x axis 510 and y axis 520 relate to the distance of sway. The peak anterior-posterior peak sway 570 is the distance between the maximum anterior and maximum posterior sway. Likewise, the mediolateral peak sway 560 is the distance between the maximum sway points in the mediolateral direction. These metrics represent the deviation around the central point, and how far the sway deviates from the center.

Figure 6A:
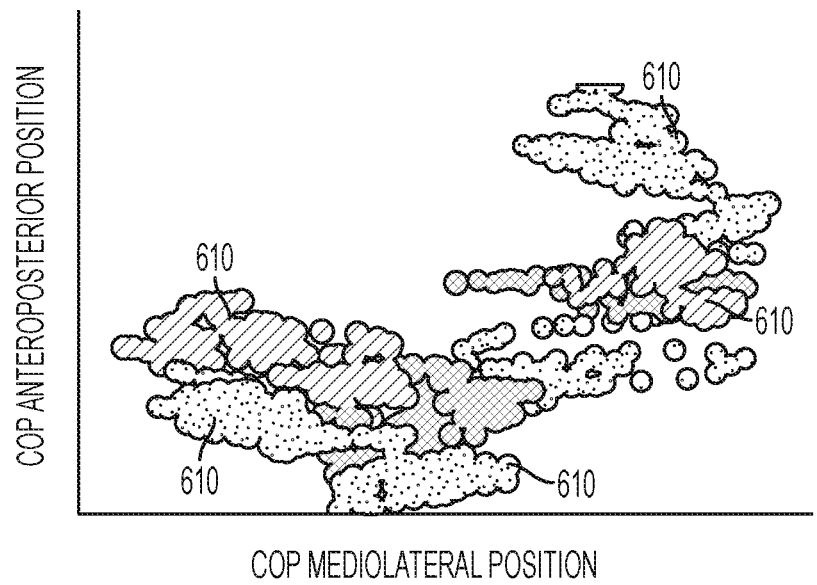
FIG. 6A is a graph illustrating data of a stabilogram of center of pressure (COP) data classified by a punctuated equilibrium model (PEM) according to one embodiment of the disclosure.
Figure 6B:
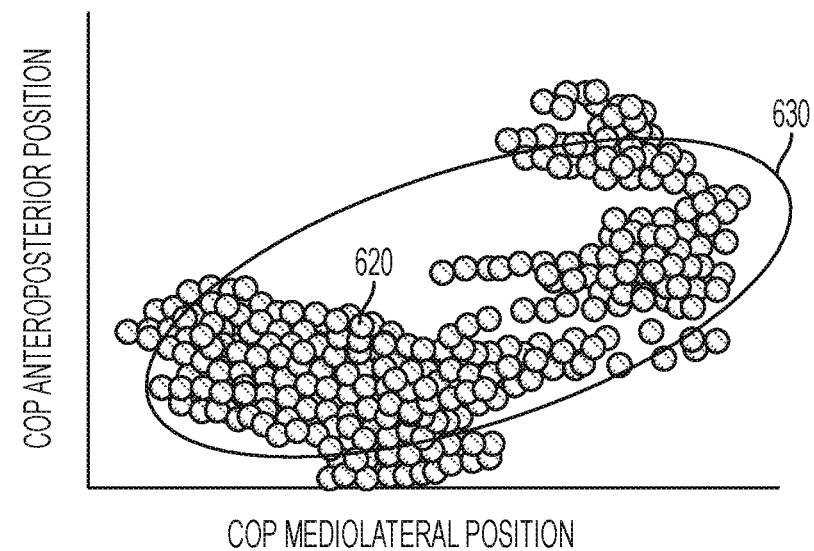
FIG. 6B shows the same stabilogram of center of pressure (COP) data as FIG. 6A represented by the single equilibrium model of postural stability with the 95% ellipse identified according to one embodiment of the disclosure.

Similarly, FIG. 6A is a graph illustrating data of a stabilogram of center of pressure (COP) data classified by a punctuated equilibrium model (PEM) according to one embodiment of the disclosure. FIG. 6B shows the same stabilogram of center of pressure (COP) data as FIG. 6A represented by the single equilibrium model of postural stability with the 95% ellipse identified according to one embodiment of the disclosure. In FIG. 6A, the pentagons have been removed, but the classified regions are clearly indicated by their differing shades of grey 610. This is in contrast with FIG. 6B, which illustrates the IPM uniform representation of the time series 620. The 95% ellipse contains 95% of all of the data points and is a representation of postural stability by the total sway area 630. Visually, it is clear to see the HMM classification provides different elements of the stabilogram. Together the metrics from both of these two models: the IPM and the HMM, may provide a more robust and comprehensive approach that neither may create in isolation.

Figure 7:
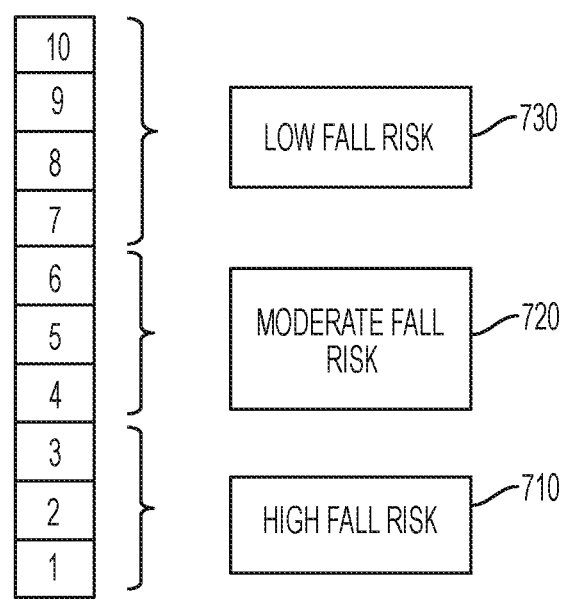
FIG. 7 is a block diagram illustrating a balance score with three fall risk classifications according to one embodiment of the disclosure.

FIG. 7 is a block diagram illustrating a balance score with three fall risk classifications according to one embodiment of the disclosure. The composite balance score 430 has a range from 1 to 10. 10 is the best balance, and 1 is the least stable. Thresholds for fall risk can be identified at block 430 and in FIG. 7 they are defined as high risk for falling 710 if the person scores 1-3, moderate risk for falling 720 if the person scores 4-6 and low risk for falling 730 if the person scores 7-10. The thresholds can also be based, in part, on injury state, mental state, cognitive state, medical state, movement state, health state, attention state, intoxicated state, and/or hypoxia state.

Figure 8:
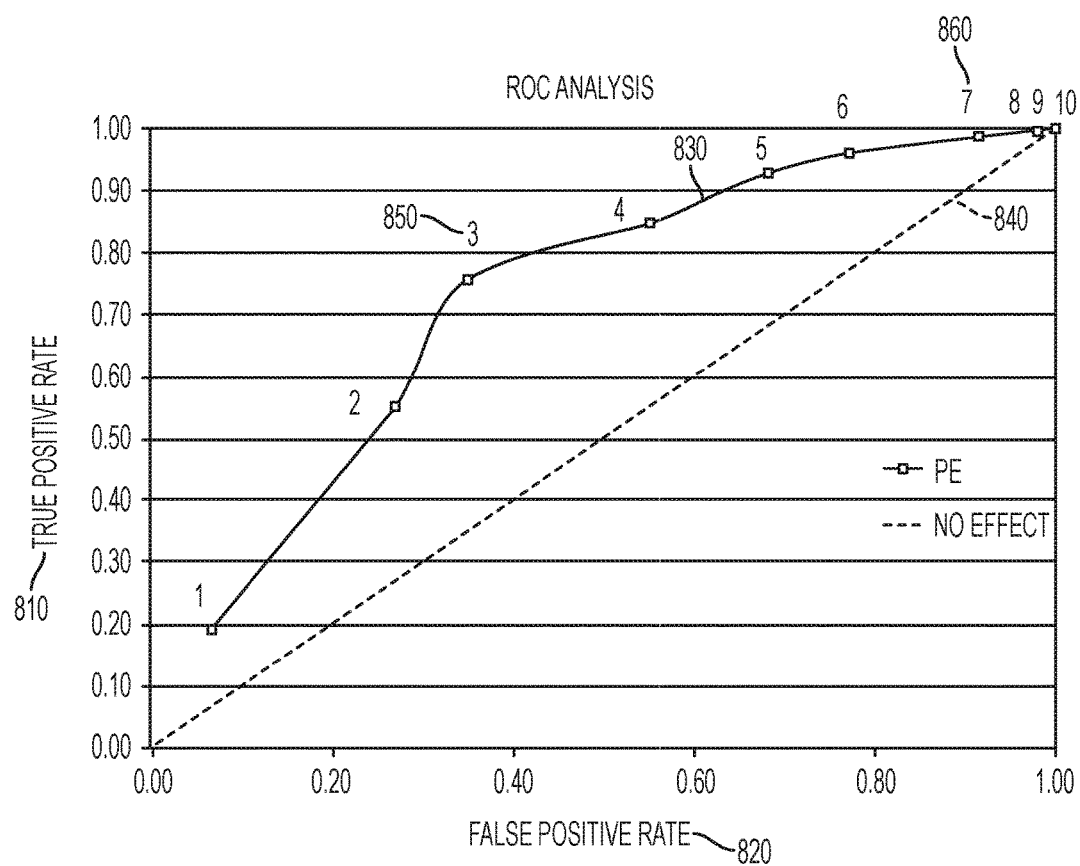
FIG. 8 is a graph showing data of a Receiver Operating Curve for identifying falls according to one embodiment of the disclosure.

FIG. 8 is a graph showing data of a Receiver Operating Curve for identifying falls according to one embodiment of the disclosure. The curve provides an evaluation of fall risk classification. These data are based on 37 subjects, with a mean age 87.09 years, and their fall history within a year. The y axis represents the accumulative true positive identification of a fall occurrence 810, and the x axis represents the accumulative identification of no falls 820. Points 1 through 10 on the PE line 830 represent each possible score of the composite balance score 430. The line of no effect 840 depicts the theoretical location of equal levels of positive and negative identification, and thereby having no discrimination capability. A clear threshold for maximizing high fall risk classification 710 occurs at score 3 850. The accumulation of score 1, and 3 yields a sensitivity for correctly classifying those at risk for falling as 76%, with a false positive rate of 35%, 65% specificity. The rate of identifying falls is minimal from 7 onwards 860 and therefore, classifies the upper, low fall risk range 730, as illustrated in FIG. 7.

Figure 9:
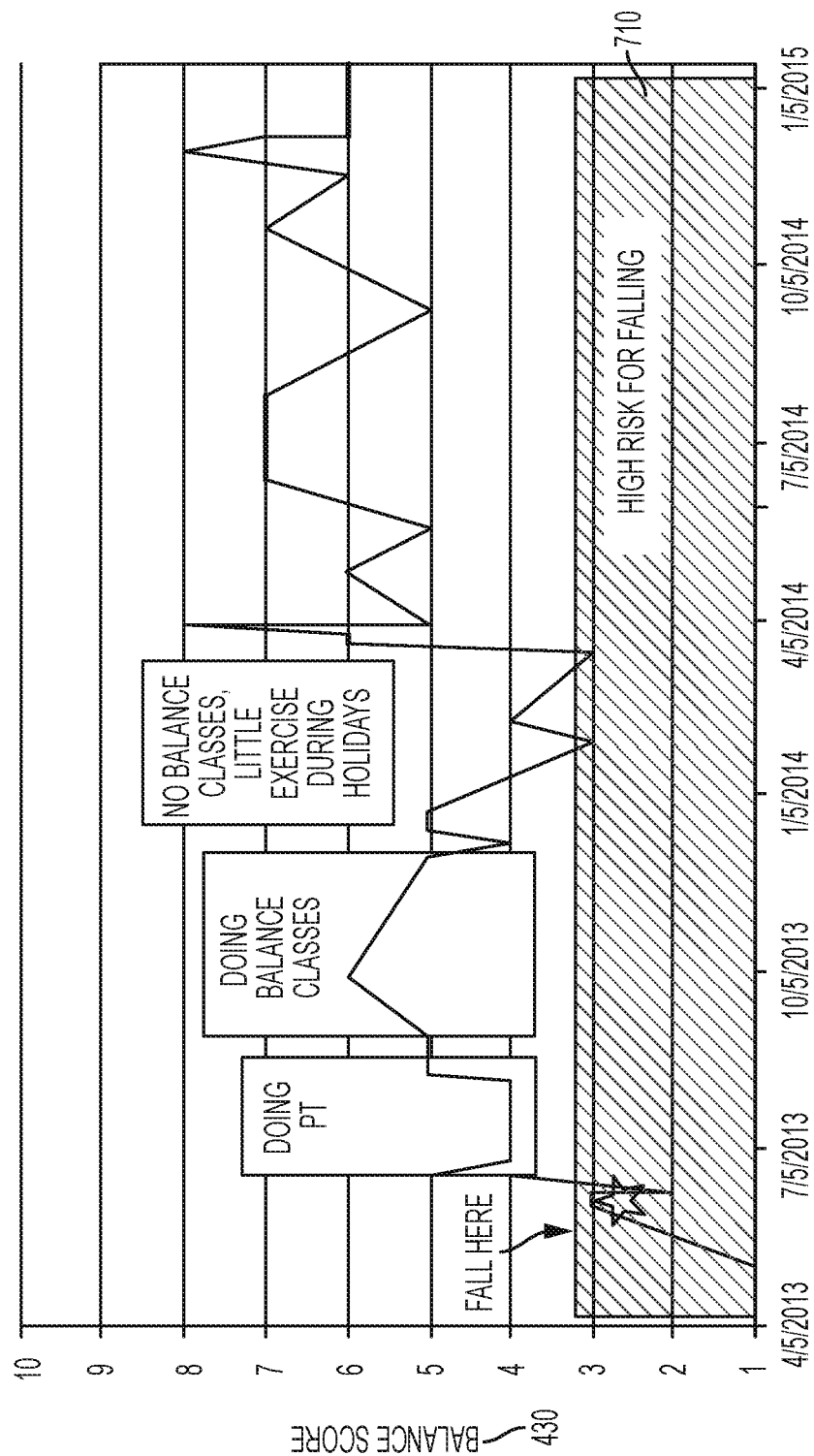
FIG. 9 is a graph showing data of an individual person's balance score and fall risk data over 2 years with annotated balance influencers according to one embodiment of the disclosure.

Furthermore, the classified output can be sensitive to subtle changes in balance created by lifestyle factors. FIG. 9 is a graph showing data of an individual person's balance score and fall risk data over two years with annotated balance influencers according to one embodiment of the disclosure. Notable periods of increased and reduced balance and fall risk are related to the participant's activity. A fall event occurred after the participant scored low and correctly identified as being at high risk for failing 710. Physical therapy (PT) was prescribed after the fall event and coincided with an elevation of the balance score and reduction of fall risk 430. The trend is maintained with specific balance classes offered in the participant's associated living facility. The end of those classes and a reduction in exercise during the New Year was associated with a lower score and greater fall risk. These data depict the value of this invention for quantifying subtle changes in fall risk and empowering people to be proactive about their health.

A system may be used for determining postural stability and fall risk for a person. The system may include components for capturing load data, processing the data as necessary, transmitting the processed data, performing additional processing of the data based on a plurality of balance-related metrics to present balance and fall risk data for the person in question, transmitting data results, and displaying the data to the user, third party provider, and/or other support personnel to advise the reader of the person's postural stability and fall risk.

Figure 10:
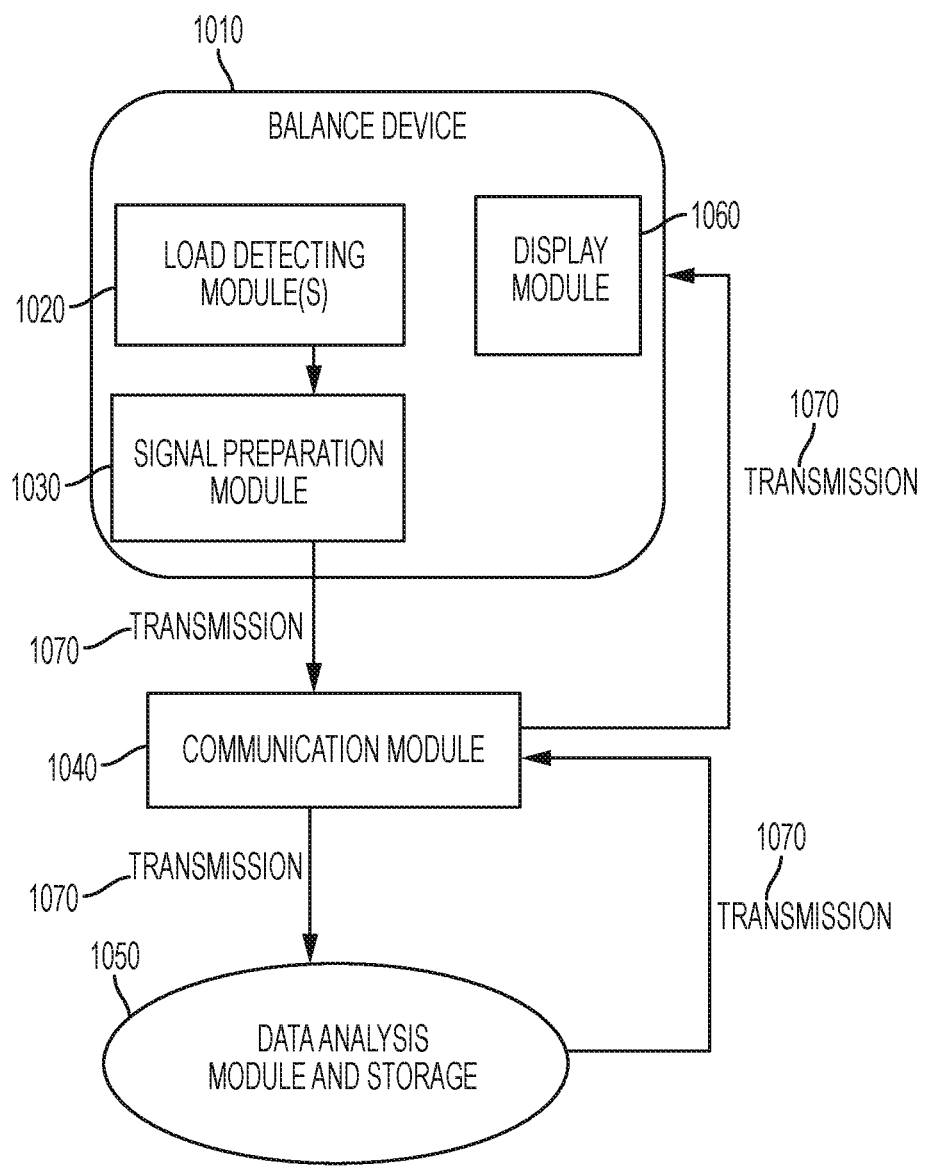
FIG. 10 is a block diagram illustrating a system and data flow throughout the system according to one embodiment of the disclosure.

FIG. 10 is a block diagram illustrating a system and data flow throughout the system according to one embodiment of the disclosure. The system includes two or more load sensors 1020 that collect load data for a period of time. The system may also include a signal preparation module 1030 housed within a balance device 1010 with wireless transmission capability for transmitting the load data 1070 to a communication module 1040 and, according to one aspect of the present invention, then to a cloud-based data analysis module 1050. The signal preparation module 1030 may contain analog-to-digital converters (ADCs), timers, and other discrete or integrated components used to convert the output of the load sensor module(s) 1020 to digital data values. The signal preparation module 1030 may include any general purpose processor, a microprocessor, amplifier, other suitably configured discrete or integrated circuit elements, and memory. The memory may be any type of volatile or non-volatile storage medium including solid-state devices such as DRAM, SRAM, FLASH, MRAM or similar components for data storage. The signal preparation module 1030 may be configured with circuitry and/or instructions to process data from the load sensors (e.g., convert analog to digital or otherwise interpret the load sensor signals) and/or package the data for transmission over a network connection or other bus (either wired or wireless), such as by forming packets or frames for network transmission or assembling data for USB transfer. A power source such as a battery (not shown) may be attached by any suitable arrangement for providing power to the circuits of the load detecting module 1020 and signal preparation module 1030.

In one embodiment, the communication module 1040 may comprise one or more integrated circuits (e.g. microcontroller, etc.) and/or discrete components on a printed circuit board or other electronic packaging technology. For example, the communication module 1040 may include a RF transceiver for transmitting and/or receiving data prepared by the signal preparation module 1030. The communication module 1040 may transmit and receive data 1070 over any type of communications link, for example, the communication module 1040 may include a wireless transceiver utilizing an RF network such as a Bluetooth network. The communication module 1040 may include authentication capability to limit transfer of data to only authorized devices. Additionally, the communication module 1040 may encrypt data before transmission 1070 in order to prevent unauthorized access to the information. In some embodiments, the communication module 1040 may include a smartphone, smartwatch, tablet, or laptop that includes the ICs, components, and/or code described above.

The data analysis module 1050 contains instructions that may be executed by a processor of the data analysis module 1050, which may be local or remote. In some embodiments, the data analysis module 1050 may be coupled to the signal preparation module 1030 to provide a single apparatus capable of processing and analyzing the COP data and displaying results. In some embodiments, the data analysis module 1050 may be a laptop, desktop or, cloud-based machine, near or remote from an apparatus with the load sensors, such that the data analysis module 1050 receives load sensor data from the communications module 1040. Even when the data analysis module 1050 is receiving data from the signal preparation module 1030, a communication module 1040 may still be present to relay results of the balance score and/or fall risk determination to a remote location, such as a medical provider.

The data analysis module 1050 may include a processor programmed to receive the load data 310 or COP data 320 from the communication module 1040, which applies machine learning techniques 330 to determine balance score and fall risk information 430. The machine learning techniques 330, including HMM may be performed on a processor. Subsequently, the processor calculates the base PEM metrics 150 (e.g., metrics that involve capturing the presence of the postural states), advanced PEM metrics 210 (e.g., metrics that involve capturing how the postural states relate to each other in space and time), and basic stability metrics 410. Advanced PEM metrics may be any metric other than the metrics 160, 170, 180. The results may be stored locally in memory with the processor and then wirelessly transmitted 1070 for display by display module 1060 or other display or other storage for later retrieval. A computer program may implement or use the machine learning and balance integration algorithm 420 described in embodiments above when executed by the data analysis module 1050. The modules 1020, 1040, and 1050 may be integrated in a single device, or split between two, three, or more devices.

FIG. 10 also illustrates an embodiment of the system and data transmission throughout the system. Load data is collected from two or more load sensors over a period of time. The collected data is processed using a processor to calculate COP. A processor implements a machine learning algorithm that calculates basic postural stability metrics 410 and PEM metrics based on HMM techniques, including base PEM stability metrics 450 and advanced PEM stability metrics 210. The processor integrates these metrics to develop a balance output, a fall risk output or both. The data can be transmitted 1070 along a hard-wired system or a wireless system. The signal preparation module 1030, communication module 1040, and data analysis module 1050 and their associated processors can be located in the balance device 1010, or across additional devices, for example, a tablet and the cloud.

In one embodiment, the collected load data 310 may be first processed in the signal preparation module 1030. The load data 310 is then wirelessly transmitted 1070 to a mobile device 1040 and then to a cloud-based data analysis module 1050. These data are processed on a processor to calculate COP 320 and subsequently, basic postural stability metrics 410, basic PEM stability metrics 350 and advanced PEM stability metrics 210. The processor integrates these metrics 420 to determine fall risk and a single balance score 430. The results are stored locally by the processor in memory and the results are wirelessly transmitted 1070 to the mobile device 1040 for display and storage, and further transmitted to the balance device 1010 for display by display module 1060. Although the display module 1060 is shown in the balance device 1010, the display module 1060 may alternatively be located in another device of the system, such as a mobile device that includes the communication module 1040 and communicates with the balance device 1010.

Figures 11A, 11B, 11C:
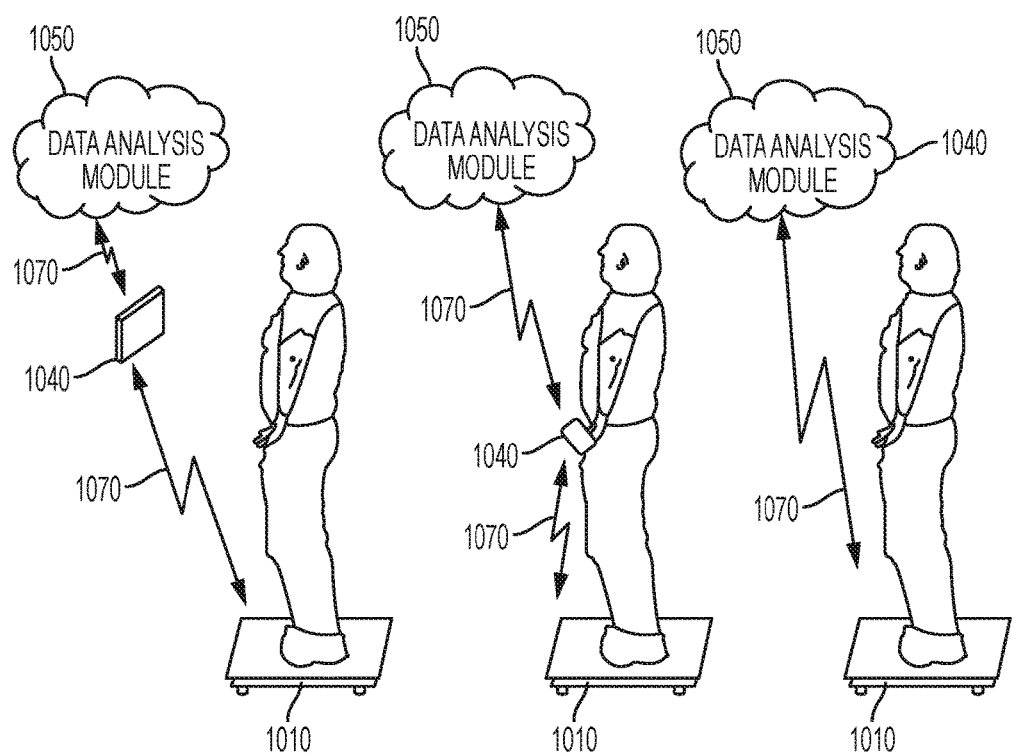
FIG. 11A is a perspective view showing the balance device communicating with a tablet according to one embodiment of the disclosure.
FIG. 11B is a perspective view showing the balance device communicating with a smart phone according to one embodiment of the disclosure.
FIG. 11C is a perspective view showing the balance device communicating with a cloud-based data analysis module according to one embodiment of the disclosure.

The balance device 1010 can be any variety of load detecting balance and fall risk devices, including a scale, mat, floor panel, shoe, insole, sock, walker, cane, prosthetic or robotic leg. The communication module 1040 can be any variety of a mobile device, smartwatch, smartphone, tablet, computer, cloud-based service and/or data analysis module. If the communication device 1040 is a tablet, the user may hold the device or have it near the scale during the test, or attached to a wall in front of the user. FIG. 11A illustrates a perspective view of a balance scale 1010 with a tablet as the communication module 1040, in accordance with one embodiment of the present invention.

If the communication device 1040 is a smartphone, the user may hold the device or have it near the scale during the test or attached to a wall in front of the user. FIG. 11B illustrates a perspective view of the balance device 1010 with a smartphone as the communication module 1040, in accordance with another embodiment of the present invention. FIG. 11C illustrates a perspective view of the balance device 1010 with a cloud-based data analysis module 1050 as the communication module 1040, in accordance with yet another embodiment of the present invention.

Figure 12:
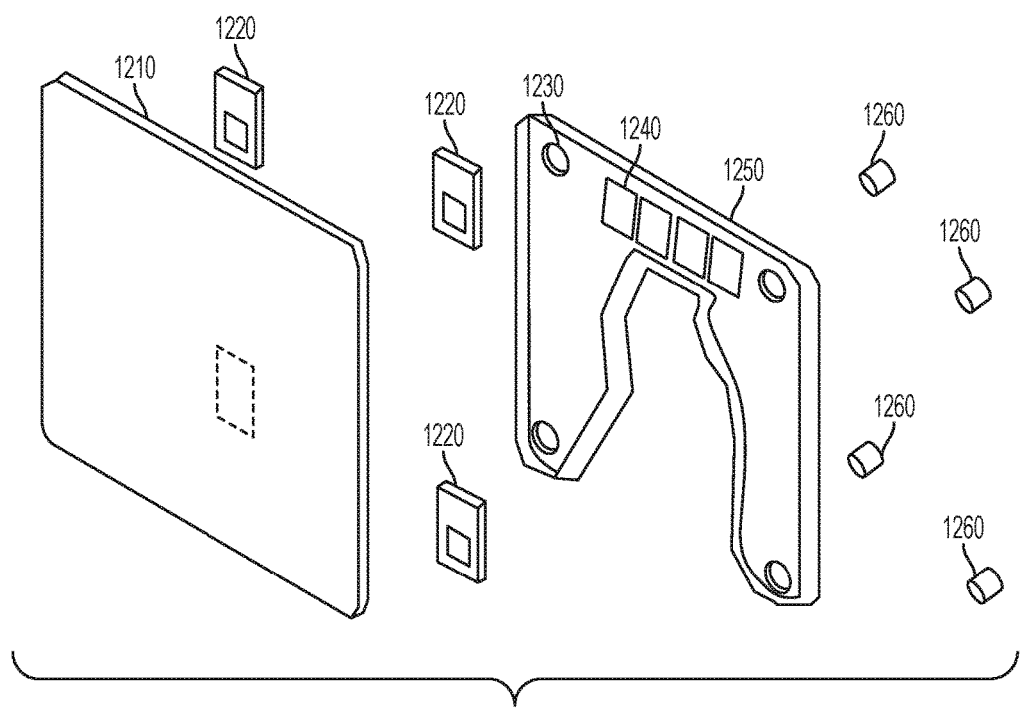
FIG. 12 is an exploded view illustrating a scale balance device according to one embodiment of the disclosure.

FIG. 12 is an exploded view illustrating a scale balance device according to one embodiment of the disclosure. In this embodiment there are 2 main layers: the top layer is glass 1210 or another semi-transparent material, and the casing 1220 is the bottom layer. The components of the load casing 1220 are housed within the casing 1250 and affix to the top layer 1210. The feet 1260 extend through the casing holes 1230. There may be no external buttons or switches on the scale, but a display of numbers 1240, functioning as part of the display module 1060, may be housed within the casing 1250.

Figure 13A:
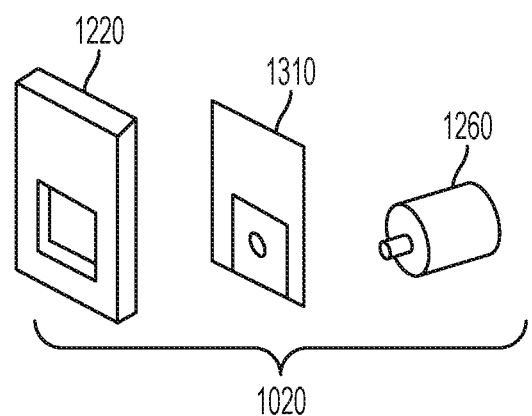
FIG. 13A is an exploded view illustrating a load detecting module according to one embodiment of the disclosure.

FIG. 13A is an exploded view illustrating a load detecting module according to one embodiment of the disclosure. The load detecting module 1020 includes load casing 1220, a load cell 1310 and foot 1260. The load cell 1310 is embedded within the load casing 1220. The load casing 1220 is affixed to the top glass layer 1210, and force is exerted through the foot 1260 enabling the load cell 1310 to deform and detect load change, in accordance with one embodiment of the present invention.

Figure 13B:
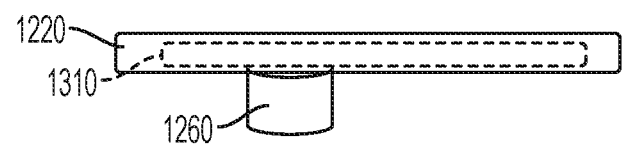
FIG. 13B is a side perspective view illustrating a load detecting module according to one embodiment of the disclosure.

FIG. 13B is a side perspective view illustrating a load detecting module according to one embodiment of the disclosure. FIG. 13B illustrates how the components of the load detecting module 1020: the foot 1260, load cell casing 1220, and load cell 1310, fit together.

Figure 14A:
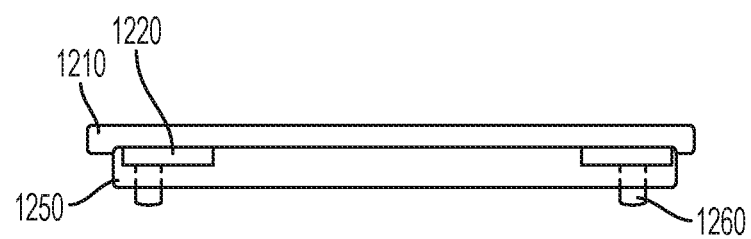
FIG. 14A is a side perspective view illustrating a scale balance device according to one embodiment of the disclosure.
Figure 14B:
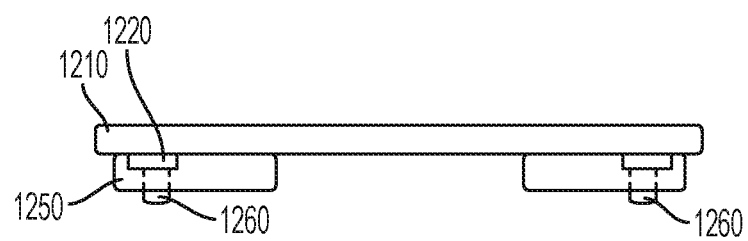
FIG. 14B is a rear perspective view illustrating a scale balance device according to one embodiment of the disclosure.

FIG. 14A is a side perspective view illustrating a scale balance device according to one embodiment of the disclosure. FIG. 14B shows a rear perspective view of one version of the balance device. In this embodiment, the casing 1250 is not completely matching the area of the top layer 1210 but, instead, is a shaped casing 1250 with partial coverage.

Figure 15:
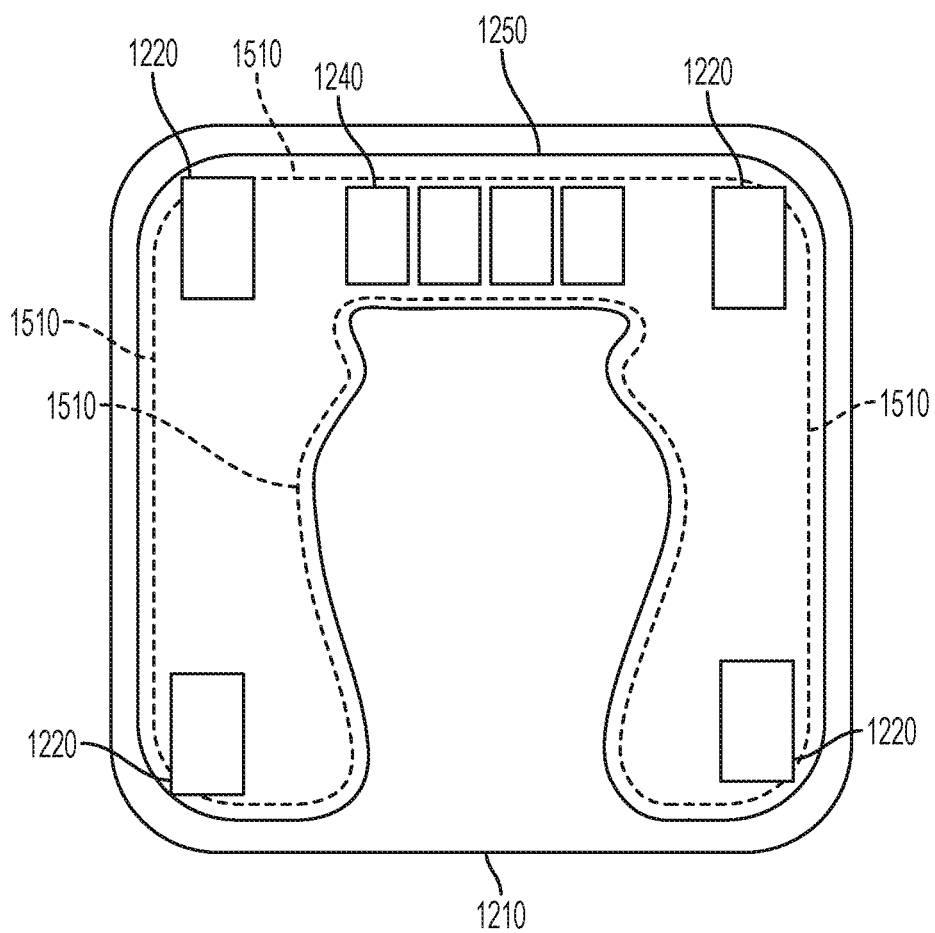
FIG. 15 is a plan view illustrating a scale balance device and display according to one embodiment of the disclosure.

FIG. 15 is a plan view illustrating a scale balance device and display according to one embodiment of the disclosure. The display module 1060 may include four 7-segment LEDs 1240 at least 2" long, and a plurality of LED lights 1510 throughout the casing to provide a glowing illumination effect through the semi-transparent top surface 1210 of the balance device 1010. The glowing illumination provides an indication of fall risk determined at block 340 of FIG. 3: red is high risk 710, yellow is moderate risk 720, and green is low risk 730 of falling, in accordance with one embodiment of the present invention. The size of the numbers 1240 and illuminating the risk factors may be sized to provide the user their result without requiring the user to bend down to see the display 1240.

Standard materials, well known in scale construction can be used to make the scale. This may include plastic injection molding for the casing 1250, load casing 1220, and feet 1260, tempered glass for the top layer 1210 that is made semi-transparent by film, etching, paint or any combination of those techniques.

In one embodiment, the balance measuring scale may be absent of any external buttons and switches so as to not require user inputs. The scale 1010 also includes illuminating numbers 1240, preferably at least about two inches long, that illuminate a visual display 1060 on a balance device 1010 that is low profile and more narrow than the width of standard walker axles. Utilizing an array of metrics from two models of postural control creates a robust measurement system for balance and fall risk detection. The outcome of which is the capability to detect balance and fall risk during a safe testing procedure, standing with eyes open, with no disruptors or sensory manipulations. Furthermore, the composite balance score 430 may simplify highly complex analytics necessary to depict postural stability to a single balance score from 1 to 10 that is easily comprehended by a user. Altogether, this system provides seniors or any users the ability to test themselves unsupervised, without either a clinician or an assistant.

In use, a user would mount the scale 1010 and adopt a comfortable standing position, keeping as still as possible. There may be a notification on the scale 1010 and/or communication module 1040 to indicate the test has commenced. In one embodiment, the test duration is 60 seconds. At the end of the test, there may be a notification sound and/or light to signify the test completion. The weight may be displayed on the scale 1010 and/or a linked mobile device. Then, the balance score may be displayed 1060 on the scale 1010 and/or the linked mobile device. The fall risk may also be displayed 1060 on the scale 1010 and/or a linked mobile device, such as via an illuminated display 1060 where color represents the risk classification.

Figure 16A:
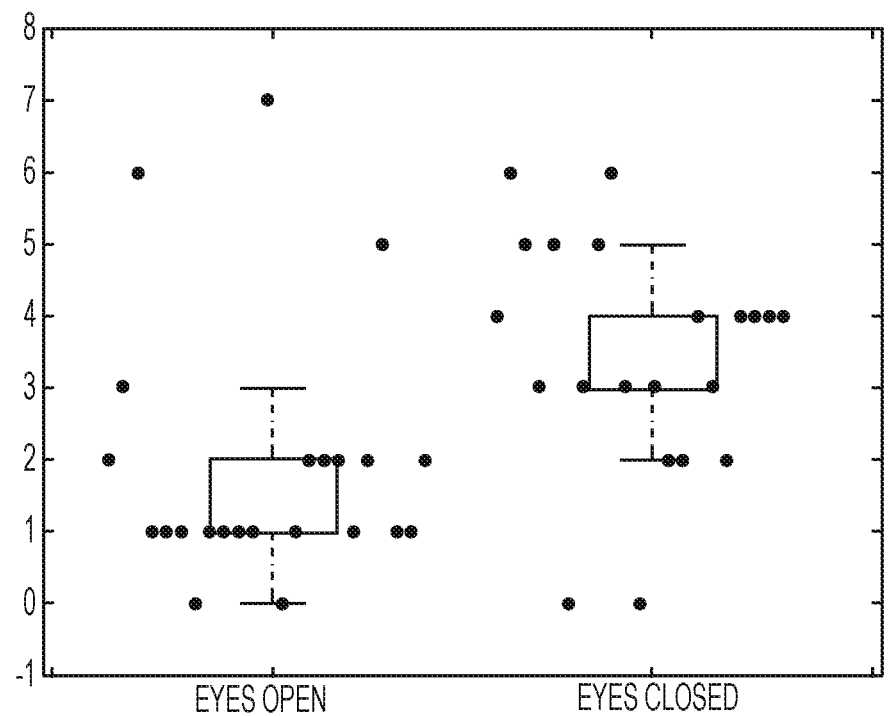
FIGS. 16A-C are graphs illustrating the results of evaluating fall risk based on individual metrics for eyes open patients and eyes closed patients.
Figure 16B:
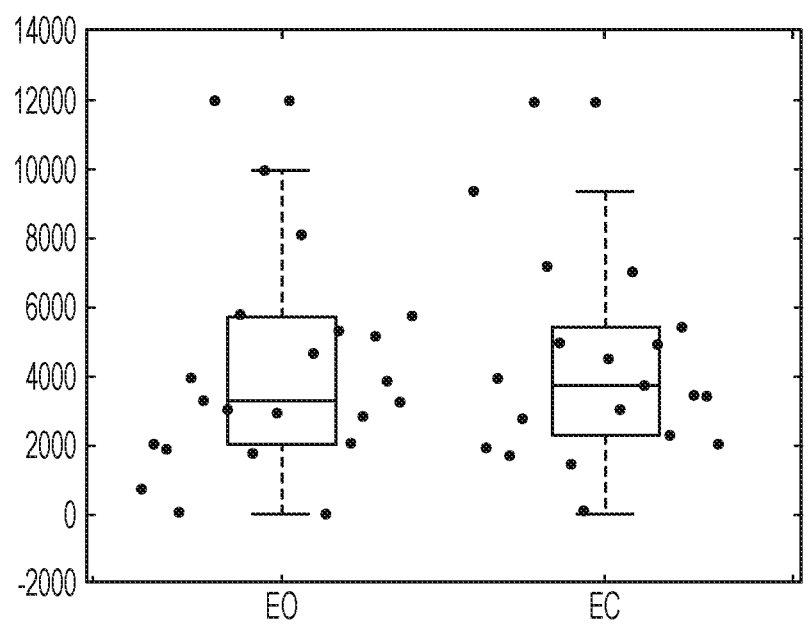
Figure 16C:
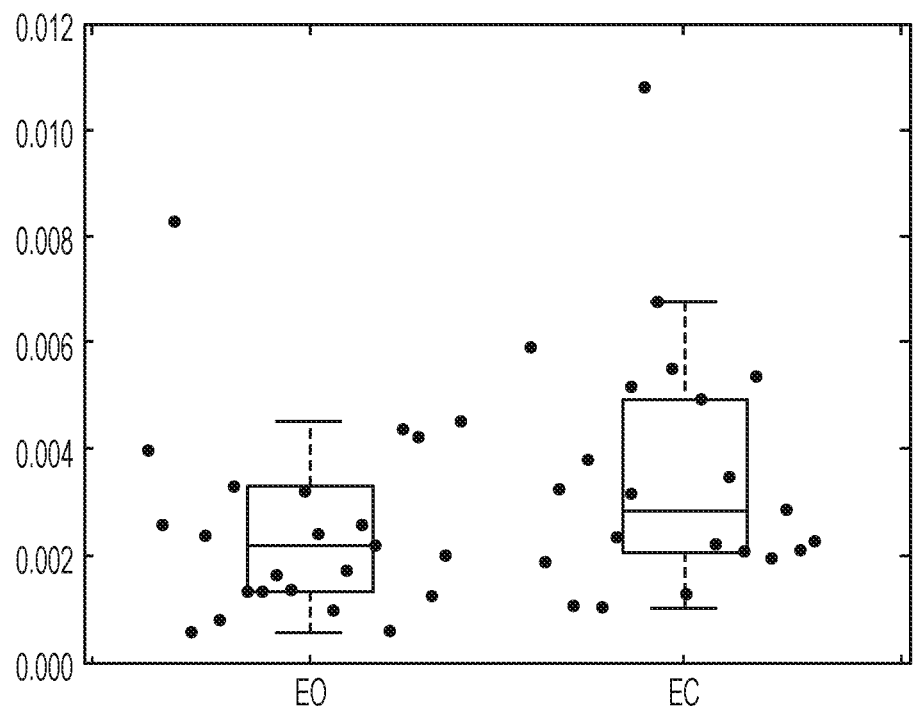

Embodiments of the invention above describe the use of a machine learning algorithm and various metrics, such as basic PEM metrics and advanced PEM metrics, to estimate an individual's fall risk. Each individual metric, whether PEM or basic, has limited discriminatory power for detecting instability when viewed in isolation. For example, FIGS. 16A-C show marginal or little difference in results between eyes open and eyes closed conditions for normal subjects for PEM metrics, such as the number of equilibrium shown in FIG. 16A, equilibrium dwell time shown in FIG. 16B, and the basic metric of 95% confidence sway ellipse shown in FIG. 16C. Consequently, it was unexpected that the same metrics when combined with advanced PEM metrics (such as metrics that take into account the relationship in time and space between postural states generated by a HMM), correctly identified individuals who are at risk of falling in a study of 78 older adults that included self-testing. The advantage of the PEM analysis is that greater dynamism is detected so a safe, eyes open standing protocol can be used and self-testing is possible without placing the individual at risk. This is in contrast to most balance tests that challenge the balance of the subject to expose weaknesses, often requiring a clinician/operator to be ready to catch to treat an individual that falls.

The schematic flow chart diagrams of FIG. 2, FIG. 3, and FIG. 4 are generally set forth as a logical flow chart diagram. As such, the depicted order and labeled steps are indicative of aspects of the disclosed method. Other steps and methods may be conceived that are equivalent in function, logic, or effect to one or more steps, or portions thereof, of the illustrated method. Additionally, the format and symbols employed are provided to explain the logical steps of the method and are understood not to limit the scope of the method. Although various arrow types and line types may be employed in the flow chart diagram, they are understood not to limit the scope of the corresponding method. Indeed, some arrows or other connectors may be used to indicate only the logical flow of the method. For instance, an arrow may indicate a waiting or monitoring period of unspecified duration between enumerated steps of the depicted method. Additionally, the order in which a particular method occurs may or may not strictly adhere to the order of the corresponding steps shown.

If implemented in firmware and/or software, functions described above may be stored as one or more instructions or code on a computer-readable medium. Examples include non-transitory computer-readable media encoded with a data structure and computer-readable media encoded with a computer program. Computer-readable media includes physical computer storage media. A storage medium may be any available medium that can be accessed by a computer. By way of example, and not limitation, such computer-readable media can comprise random access memory (RAM), read-only memory (ROM), electrically-erasable programmable read-only memory (EEPROM), compact disc read-only memory (CD-ROM) or other optical disk storage, magnetic disk storage or other magnetic storage devices, or any other medium that can be used to store desired program code in the form of instructions or data structures and that can be accessed by a computer. Disk and disc includes compact discs (CD), laser discs, optical discs, digital versatile discs (DVD), floppy disks and Blu-ray discs. Generally, disks reproduce data magnetically, and discs reproduce data optically. Combinations of the above should also be included within the scope of computer-readable media.

In addition to storage on computer readable medium, instructions and/or data may be provided as signals on transmission media included in a communication apparatus. For example, a communication apparatus may include a transceiver having signals indicative of instructions and data. The instructions and data are configured to cause one or more processors to implement the functions outlined in the claims.

Although the present disclosure and certain representative advantages have been described in detail, it should be understood that various changes, substitutions and alterations can be made herein without departing from the spirit and scope of the disclosure as defined by the appended claims. Moreover, the scope of the present application is not intended to be limited to the particular embodiments of the process, machine, manufacture, composition of matter, means, methods and steps described in the specification. For example, although processors are described throughout the detailed description, aspects of the invention may be executed by any type of processor, including graphics processing units (GPUs), central processing units (CPUs), digital signal processors (DSPs), application-specific integrated circuits (ASICs), and/or other circuitry configured to execute firmware or software that executes the instructions and methods described above. As one of ordinary skill in the art will readily appreciate from the present disclosure, processes, machines, manufacture, compositions of matter, means, methods, or steps, presently existing or later to be developed that perform substantially the same function or achieve substantially the same result as the corresponding embodiments described herein may be utilized. Accordingly, the appended claims are intended to include within their scope such processes, machines, manufacture, compositions of matter, means, methods, or steps.

What is claimed is:

1. A method, comprising:
   receiving, by a processor, a plurality of load data points over a period of time from at least two load detecting modules; and
   estimating, by the processor, a fall risk by applying a machine learning algorithm to the plurality of load data points, wherein the step of estimating the fall risk comprises:
      calculating center of pressure (COP) data based, at least in part, on the plurality of load data points;
      determining a plurality of posture states identified with Hidden Markov Model techniques based, at least in part, on the center of pressure (COP) data;
      calculating one or more base punctuated equilibrium model (PEM) stability metrics based, at least in part, on the plurality of posture states, wherein the base punctuated equilibrium model (PEM) stability metrics comprise metrics corresponding to a presence of a plurality of postural states;
      calculating one or more advanced punctuated equilibrium model (PEM) stability metrics based, at least in part, on the plurality of posture states, wherein the advanced punctuated equilibrium model (PEM) stability metrics comprise metrics corresponding to a relationship over space and time between the plurality of postural states; and
      determining the fall risk based, at least in part, on the one or more base punctuated equilibrium model (PEM) stability metrics and on the one or more advanced punctuated equilibrium model (PEM) stability metrics.

2. The method of claim 1, wherein the step of estimating the fall risk further comprises calculating at least one basic non-PEM metric from COP.

3. The method of claim 2, wherein the at least one basic non-PEM metric comprises at least one of COP speed, peak mediolateral sway, peak anterior-posterior sway, standard deviation of mediolateral sway, standard deviation of anterior-posterior sway, mean speed, fraction of trial above a predetermined speed, radius of a 95% sway ellipse, radius of a 95% sway circle, and root mean square (RMS) speed.

4. The method of claim 2, further comprising calculating a balance score by linearly integrating weighted metrics of the one or more base PEM stability metrics, the one or more advanced PEM stability metrics, and the at least one basic non-PEM metric.

5. The method of claim 1, wherein the one or more base PEM stability metrics comprise at least one of a number of equilibria, a dwell time in an equilibrium, and a size of each equilibrium.

6. The method of claim 1, wherein the advanced PEM stability metrics comprise at least one of a time to equilibrium, an equilibrium distance, an equilibrium overlap, a percent equilibrium, a mean equilibria duration, and directional equilibria.

7. The method of claim 1, further comprising the further step of classifying the fall risk, wherein the fall risk classification is based on classification thresholds comprising at least high risk, moderate risk, and low risk.

8. The method of claim 1, where in the step of estimating the fall risk comprises applying the machine learning algorithm with at least one of clinical records, exercise, lifestyle inputs, weight, body fat composition, body mass index, level of hydration, medication consumption, alcohol consumption, sleep, steps per day, exercise, time spent sitting, and strength.

9. The method of claim 1, wherein the step of acquiring comprises acquiring the plurality of load data points from at a load sensor on at least one of a scale, floor panel, mat, shoe, insole, sock, walker, walking aid, ladder, cane, prosthetic, and robotic leg.

10. The method of claim 1, wherein the step of estimating the fall risk further comprises determining a postural at a point in time based on at least the plurality of postural states and a probability of transitioning between at least one of the plurality of postural states and another postural state, wherein the postural state is at least one of a static postural state or a dynamic postural state.

11. A system for determining postural stability and fall risk of a person, comprising:
    two or more load detecting modules configured to acquire a plurality of load data points;
    a signal preparation module coupled to the load detecting modules and configured to convert the plurality of load data points to a transmittable form;
    a communication module coupled to the signal preparation module, the communication module configured to:
       receive the plurality of load data points from the signal preparation module;
       transmit the plurality of load data points; and
    a data analysis module configured to analyze the plurality of load data points received from the signal preparation module, wherein the data analysis module is configured to perform steps comprising:
       calculating center of pressure (COP) data based, at least in part, on the plurality of load data points;
       determining a plurality of posture states identified with Hidden Markov Model techniques based, at least in part, on the center of pressure (COP) data;
       calculating one or more base punctuated equilibrium model (PEM) stability metrics based, at least in part, on the plurality of posture states;
       calculating one or more advanced punctuated equilibrium model (PEM) stability metrics based, at least in part, on the plurality of posture states, wherein the base punctuated equilibrium model (PEM) stability metrics comprise metrics corresponding to a presence of a plurality of postural states; and
       determining the fall risk based, at least in part, on the one or more base punctuated equilibrium model (PEM) stability metrics and on the one or more advanced punctuated equilibrium model (PEM) stability metrics, wherein the advanced punctuated equilibrium model (PEM) stability metrics comprise metrics corresponding to a relationship over space and time between the plurality of postural states; and a display module coupled to the data analysis module and configured to display results from the data analysis module comprising at least an indication of the fall risk.

12. The system of claim 11, wherein the two or more load detecting modules comprise four load detecting modules, wherein the four load detecting modules are housed within a casing with a transparent or semi-transparent top layer.

13. The system of claim 12, wherein the display module comprises an illumination of the results, visible through part or all of the top layer.

14. The system of claim 11, wherein the display module comprises a plurality of LED light rows that produce a glow effect in at least one of red, yellow, green, blue, and white.

15. The system of claim 11, wherein the communication module is part of at least one of a mobile device, smartwatch, smartphone, tablet, computer, and wearable.

16. An apparatus, comprising:
two or more load detecting modules configured to acquire a plurality of load data points;
a signal preparation module coupled to the load detecting modules and configured to convert the plurality of load data points to a transmittable form;
a communications module coupled to the signal preparation module and configured to:
transmit the plurality of load data points to a data analysis module; and
receive, from the data analysis module, a fall risk calculated by a machine learning algorithm based, at least in part, on one or more base punctuated equilibrium model (PEM) stability metrics and on one or more advanced punctuated equilibrium model (PEM) stability metrics,
wherein the base punctuated equilibrium model (PEM) stability metrics comprise metrics corresponding to a presence of a plurality of postural states, and
wherein the advanced punctuated equilibrium model (PEM) stability metrics comprise metrics corresponding to a relationship over space and time between the plurality of postural states; and
a display module configured to display an indication of the received fall risk.

17. The apparatus of claim 16, wherein the two or more load detecting modules are housed within a casing with a transparent or semi-transparent top layer, and wherein the display module comprises an illumination of the fall risk, visible through part or all of the top layer.

18. The apparatus of claim 16, wherein the display module comprises a plurality of LED lights that produce a glow effect corresponding to a classification of the fall risk.

19. The apparatus of claim 16, wherein the communications module is configured to communicate with the data analysis module through a mobile device.

20. The apparatus of claim 16, wherein the communications module is configured to communicate with the data analysis module through the Internet.

* * * * *